(12) United States Patent
Rosset

(10) Patent No.: US 10,987,442 B2
(45) Date of Patent: Apr. 27, 2021

(54) INFORMATION MEDIUM HAVING ANTIVIRAL PROPERTIES, AND METHOD FOR MAKING SAME

(75) Inventor: Henri Rosset, Le Pin (FR)

(73) Assignee: OBERTHUR FIDUCIAIRE SAS, Paris (FR)

( * ) Notice: Subject to any disclaimer, the term of this patent is extended or adjusted under 35 U.S.C. 154(b) by 0 days.

(21) Appl. No.: 13/319,010

(22) PCT Filed: May 7, 2010

(86) PCT No.: PCT/IB2010/052028
§ 371 (c)(1),
(2), (4) Date: Jan. 17, 2012

(87) PCT Pub. No.: WO2010/128487
PCT Pub. Date: Nov. 11, 2010

(65) Prior Publication Data
US 2012/0114725 A1 May 10, 2012

(30) Foreign Application Priority Data
May 7, 2009 (FR) .................................. FR0953053

(51) Int. Cl.
*A01N 31/02* (2006.01)
*B42D 25/29* (2014.01)
*A61L 2/16* (2006.01)

(52) U.S. Cl.
CPC ................. *A61L 2/16* (2013.01); *A01N 31/02* (2013.01); *B42D 25/29* (2014.10)

(58) Field of Classification Search
CPC ........ B42D 25/00; B42D 25/23; B42D 25/24; B42D 25/25; B42D 25/26; B42D 25/27; B42D 25/28; B42D 25/285; B42D 25/29; B42D 25/36; A01N 31/00; A01N 31/02; A01N 31/04
See application file for complete search history.

(56) References Cited

U.S. PATENT DOCUMENTS

| 1,996,707 | A | * | 4/1935 | Nathansohn ........... D21H 17/14 162/159 |
|---|---|---|---|---|
| 3,738,995 | A | | 6/1973 | Adams |
| 4,570,629 | A | | 2/1986 | Widra |
| 4,662,403 | A | | 5/1987 | Hammer et al. |
| 4,764,418 | A | | 8/1988 | Kuenn et al. |
| 4,908,209 | A | | 3/1990 | McIntosh, Jr. et al. |
| 4,929,498 | A | | 5/1990 | Suskind et al. |
| 4,950,685 | A | | 8/1990 | Ward |
| 5,039,339 | A | | 8/1991 | Phan et al. |
| 5,177,128 | A | | 1/1993 | Lindemann et al. |
| 5,217,576 | A | | 6/1993 | Van Phan |
| 5,709,870 | A | | 1/1998 | Yoshimura et al. |
| 5,709,976 | A | | 1/1998 | Malhotra |
| 5,786,282 | A | | 7/1998 | Carter et al. |
| 5,968,538 | A | | 10/1999 | Snyder, Jr. |
| 6,197,805 | B1 | | 3/2001 | Smith |
| 6,262,097 | B1 | | 7/2001 | Kovacevic |
| 6,524,508 | B1 | | 2/2003 | Ohnishi et al. |
| 8,193,244 | B1 | * | 6/2012 | Stockel et al. ................. 514/529 |
| 2002/0068013 | A1 | | 6/2002 | Wilcox et al. |
| 2004/0023008 | A1 | | 2/2004 | Rosset |
| 2004/0109853 | A1 | | 6/2004 | McDaniel |
| 2005/0043402 | A1 | | 2/2005 | Thormar et al. |
| 2005/0175712 | A1 | * | 8/2005 | Jayet-Laraffe et al. ........ 424/618 |
| 2006/0030512 | A1 | * | 2/2006 | Hart .............................. 510/481 |
| 2008/0171804 | A1 | | 7/2008 | Krishnan |
| 2008/0279959 | A1 | | 11/2008 | Holmes |
| 2009/0105195 | A1 | | 4/2009 | O'Brien |
| 2010/0056628 | A1 | | 3/2010 | Stockel et al. |
| 2014/0155482 | A1 | | 6/2014 | Rosset |

FOREIGN PATENT DOCUMENTS

| CN | 101698769 A | 4/2010 |
|---|---|---|
| EP | 0 059 056 | 9/1982 |
| EP | 0251132 A1 | 1/1988 |
| EP | 0191217 B1 | 3/1988 |
| EP | 0749848 A1 | 12/1996 |
| EP | 0866103 A1 | 9/1998 |
| EP | 1138314 A2 | 10/2001 |
| EP | 2160946 A1 * | 9/2008 |
| JP | 51101124 A | 9/1976 |
| JP | 54 041326 A | 4/1979 |
| JP | 61181390 A | 8/1986 |
| JP | 91181390 A | 8/1986 |
| JP | 04356404 A | 12/1992 |
| JP | 05139918 A | 6/1993 |
| JP | 017-292742 | 11/1995 |
| JP | 0967797 A | 3/1997 |
| JP | 09119096 A | 5/1997 |

(Continued)

OTHER PUBLICATIONS

Pereira et al. Enzymatic Synthesis of Monolaurin. pp. 433-445. Proceedings of the Twenty-Fifth Symposium on Biotechnology for Fuels and Chemicals Held May 4-7, 2003, in Breckenridge, CO. 2004. (Abstract Only).*
Marqez-Alwarez et al. Solid catalysts for the synthesis of fatty esters of glycerol, polyglycerols and sorbitol from renewable resources. Topics in Catalysis. 2004. vol. 27(1-4) pp. 105-117.*
Argy et al. Study of prophylaxis by didecyl dimethyl ammonium chloride against herpes simplex virus infection in nude mice. C R Acad Sci III. Oct. 1999;322(10):863-70. abstract only.*
Pereira et al. Enzymatic synthesis of monolaurin. Applied Biochemistry and Biotechnology, 2004, vol. 113-116.*
Dawson et al. Effect of lauric acid and nisin-impregnated soy-based films in the growth of Listeria monocytogeners on turkey bologna. Poultry Science, vol. 81:5 (721-726). (Year: 2002).*
Hierholzer et al. In vitro effects of monolaurin compounds on enveloped RNA and DNA viruses.Journal of Food Safety, 1-2, pp. 1-12 (Year: 1982).*

(Continued)

*Primary Examiner* — Lakshmi S Channavajjala
(74) *Attorney, Agent, or Firm* — Jones Robb, PLLC

(57) ABSTRACT

The present invention relates to an information medium to be handled by a large number of users, such as a banknote, and having antiviral properties, and to a method for making same.

14 Claims, No Drawings

(56) References Cited

FOREIGN PATENT DOCUMENTS

| | | |
|---|---|---|
| JP | 10259326 A | 9/1998 |
| JP | 11071211 A | 3/1999 |
| JP | 2009527357 A | 7/2009 |
| RU | 92012302 A | 11/1995 |
| RU | 2 181 583 C1 | 4/2002 |
| RU | 2195473 C1 | 12/2002 |
| RU | 2303615 C1 | 7/2007 |
| RU | 2338765 C1 | 11/2008 |
| WO | WO9942658 A1 | 8/1999 |
| WO | WO0018577 A1 | 4/2000 |
| WO | WO0049219 A1 | 8/2000 |
| WO | WO 00/71183 A1 | 11/2000 |
| WO | WO 03/084326 A2 | 10/2003 |
| WO | WO 2005/022998 A2 | 3/2005 |
| WO | 2005056449 A1 | 6/2005 |
| WO | 2006008566 A1 | 1/2006 |
| WO | WO 2007/044398 A2 | 4/2007 |
| WO | 2007100654 A2 | 9/2007 |
| WO | 2008127416 A2 | 10/2008 |
| WO | 2010128487 A2 | 11/2010 |

OTHER PUBLICATIONS

Clarke, N. M. et al.: "Effect of Antimicrobial Factors in Human Milk on Rhinoviruses and Milk-Bourne Cytomegalovirus in vitro," Journal of Medicinal Microbiology, vol. 49, Jun. 30, 2000, pp. 719-723.

Loizzo, M. R.: "Phytochemical Analysis and in vitro Antiviral Activities of the Essential Oils of Seven Lebanon Species," Chemistry and Biodiversity, vol. 5, Mar. 20, 2008, pp. 461-470.

Seganti, L., et al.: "Antiviral Activity of Lactoferrin Towards Naked Viruses," Biometals, Kluwer Academic Publishers, BO, vol. 17, No. 3, Jun. 1, 2004, pp. 295-299.

International Search Report and Written Opinion for International Application No. PCT/IB2010/052028 dated May 4, 2011.

Preliminary Search Report and Written Opinion for French Priority Application No. 09 53053 dated Nov. 30, 2009.

Dreikom, "Agricultural Fungicides," (1994) and McEntee, "Industrial Antimicrobial Agents," (1995) in Kirk-Othmer Encyclopedia of Chemical Technology, Wiley, 2000 Online Edition.

American Society for Testing and Materials, "Test method for determining the antimicrobial activity of immobilized antimicrobial agents under dynamic contact conditions," ASTM Method E 2149-01, vol. 11.05, 2001.

Association Francaise de Normalisation, "Characterization and measurement of the bacteriostatic activity of fabrics and polymer surfaces with antibacterial properties," AFNOR Method XP G39-010, May 2000.

Environmental impact of euro banknotes' from the European Central Bank, Dec. 20, 2007.

Kumar "A review of chitin and chitosan applications", Reactive and Functional Polymers, 2000, vol. 46, pp. 1-27.

(English Abstract of) "Enzymatic synthesis of decanoic acid monoglycerides", Chinese Journal of Process Engineering, vol. 4, No. 1, Feb. 2004.

(English Translation of) Office Action issued in the corresponding Chinese proceeding dated Jan. 7, 2015.

Lieberman, et al. "A review of Monolaurin and lauric acid, Alternative & complementary therapies", Dec. 2006, vol. 12, pp. 310-315.

Preuss, et al. "Effects of Essential Oils and Monolaurin on *Staphylococcus aures*: In vitro and in Vivo Studies, Toxicology mechanisms and methods", vol. 15, pp. 279-285.

European Office Action for corresonding Application No. 11 797 364.4, dated Oct. 31, 2016.

International Search Report & Written Opinion for PCT/IB2011/054927, dated Mar. 20, 2012.

Mosselman, Chemical Data sheet for Glyceryl Monolaurate > 90% Belgium, Date Accessed Sep. 27, 2016. www.mosselman.be.

Ozcan, "Antimicrobial activity of the essential oils of Turkish plant spices", Eur. Food Res. Technol., 2001, 212, pp. 658-660.

Preliminary Search Report & Written Opinion for Application No. FA 744247 and FR 10591295, dated Nov. 8, 2010.

Republic of Kazakhstan office action for Application No. 2013/1552.1 filed on Apr. 11, 2011.

Thormar, et al. "Inactivation of Enveloped Viruses and Killing of Cells by Fatty Acids and Monoglycerides", Antimicrobial Agents oand Chemotherapy, Jan. 1987, vol. 31, No. 1, pp. 27-31.

Tipvarakarnkoon, et al. Rheological properties and phase change behaviors of coconut fats and oils, Annual Transactions of the Nordic Rheology Society, 2008, vol. 16, 17 pgs.

\* cited by examiner

INFORMATION MEDIUM HAVING ANTIVIRAL PROPERTIES, AND METHOD FOR MAKING SAME This is a national stage application of PCT/2010/052028, filed internationally on May 7, 2010, which claims priority to French Application No. FR 0953053, filed on May 7, 2009.

The invention relates to an information medium intended to be handled by a large number of users, such as, for example, a banknote.

The invention aims more particularly to propose an information medium of this type which also advantageously has antiviral properties, and also the method for producing same.

In modern societies, an increasingly large amount of media for transmitting information is handled daily and frequently by a large number of individuals, for whom no health control is required.

As it happens, these individuals, owing to their environment, to their occupational activity, to their entourage and/or to the healthiness of their lifestyle, may carry viruses, capable of generating more or less serious epidemic and pandemic diseases and, in this respect, be capable of contaminating any medium with which they come into contact.

In the event that this medium is, by virtue of its nature, in turn going to be in circulation, it then itself becomes an important vehicle of virus dissemination and can potentially cause infections in those who handle it.

In addition, in recent times, since the possibility of a terrorist attack by viral contamination of information media is no longer to be ignored, the risk associated with handling these information media is becoming particularly tangible.

As exchange currency during commercial transactions, the banknote constitutes one of the most widely handled information media in the world and as a result represents a potential health threat.

It constitutes in itself a potential vector for transmission of diseases and can, with regard to those who handle it, lead to various infections that can be exacerbated depending on the amounts of pathogenic agents, on the virulence of the sample, and on individual resistance.

For example, banknotes could contribute to promoting flu epidemics. Thus, a recent study has demonstrated that flu viruses can survive for up to 17 days on a conventional banknote.

Patent application WO 03/084326 envisions the addition of a bacteriostatic and/or bactericidal and fungistatic and/or fungicidal agent to such an information medium.

However, there remains a need for effective information media for specifically combating viruses, and avoiding any risk of viral transmission and contamination.

There also remains a need for information media which have an antiviral activity while at the same time not posing any danger to the user, and in particular not using toxic and/or dangerous compounds as virucide.

It is also desirable to have information media which have a long-lasting antiviral activity.

It is also desirable to have information media of which the antiviral activity remains preferentially attached to the information medium.

The invention aims to provide an information medium which has antiviral properties and which meets these needs.

The applicant, after having tested numerous virucidal compositions, has succeeded, surprisingly, in solving the stated problems by treating the information medium using a virucide of natural origin.

Thus, according to one of its aspects, the invention relates to an information medium intended to be handled relatively frequently, characterized in that it contains an effective amount of at least one virucide of natural origin and at least one humectant.

Such a medium can thus be described as an information medium with antiviral properties, i.e. with an ability to be active against viruses.

The virucides used according to the invention advantageously do not exhibit any particular toxicity to the individuals who come to handle them and are not subject to particular guidelines.

According to another of its aspects, the invention also relates to a method for producing an information medium as defined above, comprising at least the step consisting in bringing a basic medium into contact, in the presence of at least one humectant, with said virucide of natural origin, or in particular a precursor thereof, under conditions suitable for the incorporation thereof at the level of said medium.

According to yet another of its aspects, the invention also relates to a method for producing an antiviral information medium, characterized in that at least one virucide of natural origin is synthesized in situ at the level of a basic medium made up of, for example, cellulosic and/or plastic materials.

It emerges from what follows, the virucidal properties of said medium are conferred thereon by the treatment of said medium with a composition comprising at least said virucide.

This treatment can be carried out during the method for preparing said medium, but also consecutively.

Thus, the virucidal properties of said medium according to the invention can be conferred thereon during the printing thereof with an ink comprising at least one virucide of natural origin, or else by depositing a varnish, in particular an overprint varnish, comprising at least one such virucide of natural origin.

Consequently, the present invention also relates to an information medium in accordance with the invention, the virucidal properties of which are conferred via an ink, printed onto said medium, said ink comprising at least said virucide of natural origin.

It also relates to an information medium in accordance with the invention, the virucidal properties of which are conferred via the presence of a varnish, in particular an overprint varnish, deposited on said medium, said varnish comprising at least said virucide of natural origin.

Information Medium Containing at Least One Virucide of Natural Origin

Information Medium

As indicated above, the information media more particularly considered in the context of the present invention are information media intended to be handled relatively frequently.

For the purpose of the invention, an "information medium intended to be handled relatively frequently" is a medium handled at least twice manually by the same individual or at least two distinct individuals. A manual handling may be composed of at least one contact, for example one grasping, by at least one part of a hand.

Thus, single-use media are not, for example, considered to be information media in accordance with the invention.

The information media in accordance with the invention are more particularly media intended for use in an ambient atmosphere.

In other words, the media considered according to the invention are not generally dedicated to use in a liquid medium and more particularly an aqueous medium.

The information medium intended to be handled relatively frequently in accordance with the invention may in particular be a security document comprising at least one security element.

The security document, and also the security elements that it comprises, for instance a security thread, a watermark, a pattern, a patch and/or a foil, can comprise one or more security elements as defined hereinafter.

Among the security elements, some are detectable by eye, in daylight or in artificial light, without the use of a particular apparatus. These security elements comprise, for example, colored fibers or planchettes, or totally or partially printed or metalized threads. These security elements are termed first-level security elements.

Other types of security elements are detectable only using a relatively simple apparatus, such as a lamp which emits in the ultraviolet (UV) or infrared (IR) range. These security elements comprise, for example, fibers, planchettes, strips, threads or particles. These security elements may or may not be visible to the naked eye, being for example luminescent under illumination from a Wood lamp emitting in a wavelength of 365 nm. These security elements are termed second-level security elements.

Yet other types of security elements require, for their detection, a more sophisticated detection apparatus. These security elements are, for example, capable of generating a specific signal when they are subjected, optionally simultaneously, to one or more external excitation sources. The automatic detection of the signal makes it possible to authenticate the document, as required. These security elements comprise, for example, tracers that are in the form of active materials, particles or fibers, capable of generating a specific signal when these tracers are subjected to an optronic, electrical, magnetic or electromagnetic excitation. These security elements are termed third-level security elements.

The security elements present within the security document and the elements that they comprise may have first-, second- or third-level security characteristics.

The information medium in accordance with the invention may comprise a substrate comprising papermaking fibers known to those skilled in the art, for example cellulose fibers (in particular cotton fibers) and/or natural organic fibers other than cellulose fibers and/or synthetic fibers, for example such as polyester or polyamide fibers, and/or optionally inorganic fibers, for example such as glass fibers.

According to one embodiment, the information medium in accordance with the invention is based on cellulose materials, in particular fibers, and in particular paper.

According to another embodiment, the information medium in accordance with the invention is based on natural organic fibers other than cellulose fibers.

According to yet another embodiment, the information medium in accordance with the invention is based on plastic materials, and in particular synthetic fibers or a plastic sheet.

The medium may also be a plastic film, and in particular a biaxially stretched film based on polyethylene, such as the Polyart® material sold by the company Arjobex. It is more particularly a sheet comprising a co-extruded medium, made from at least one polymer material, comprising, for example, a core layer and at least one skin layer, the core layer comprising voids.

The medium may also be a multilayer medium, in particular laminated or glued. Said multilayer medium comprises in particular at least one layer based on cellulose or plastic materials as described above.

According to yet another embodiment, the information medium in accordance with the invention is based on inorganic fibers.

The information medium considered according to the invention may be a passport, an identity card, a driver's license, an access card, a loyalty card, a photocopier card, a canteen card, a playing card, a collectable card, a means of payment, in particular a payment card, a banknote, a purchase slip or a receipt, a ticket for entry into a cultural or sporting event, a certificate of authenticity, or else packaging, a book, a geographic map, a label, an envelope or a magazine.

Preferably, the information medium in accordance with the invention is a security document, and in particular a banknote.

Virucide of Natural Origin

The information medium in accordance with the invention contains at least one virucide of natural origin.

For the purpose of the present invention, the term "virucide" denotes any compound which has the ability to kill or to inhibit viruses.

The virucide according to the present invention is more particularly dedicated to killing and/or inhibiting a virus which is pathogenic with regard to mammals, and more particularly to humans. Such viruses may be naked viruses or enveloped viruses.

By way of representation of viruses which are pathogenic to humans which can be considered according to the invention, mention may more particularly be made of retroviruses, cytomegaloviruses, rotaviruses, paramyxoviruses, polioviruses, hantaviruses, coxsackie viruses, the encephalomyocarditis virus, picornaviruses, including rhinoviruses, DNA viruses or RNA viruses, in particular flaviviridae, the AIDS virus, flu viruses, the smallpox virus, the yellow fever virus, the hepatitis C virus, herpes viruses, the Epstein-Barr virus, the varicella-zoster virus, the rubella virus, or else the simian virus 40 or SV40.

The term "virucide of natural origin" is intended to denote any virucide that pre-exists naturally or that can be synthesized from natural compounds that exist in nature.

The virucides of natural origin that can be used in the context of the present invention can thus be obtained either by extraction and purification from a natural medium containing them, or by synthesis from natural compounds.

By way of example of such virucides, mention may in particular be made of monolaurin which can be obtained by synthesis from glycerol and from lauric acid.

In the case of this second alternative, the glycerol and the lauric acid constitute, for the purpose of the invention, a virucide precursor since they make it possible, at the end of the method according to the invention, to generate a medium with antiviral properties.

More specifically, the term "precursor" denotes, according to the invention, a compound which is able, during the steps of the method according to the invention, either by conversion or by reaction with another compound which is associated therewith and therefore which is also described as a precursor, to generate the expected virucide.

According to one embodiment, the virucide of natural origin may in particular be chosen from monolaurin, lactoferrin and essential oils having an antiviral activity, for instance a bay laurel essential oil.

For the purpose of the invention, the term "monolaurin" is intended to denote both naturally pre-existing monolaurin and that obtained by synthesis from glycerol and from lauric acid.

These three types of virucide of natural origin have in fact been identified as having particularly advantageous properties for the preparation of information media as considered in the context of the present invention.

The information medium in accordance with the invention contains an effective amount of at least one virucide of natural origin, i.e. a sufficient amount of said virucide to give the information medium incorporating it antiviral properties.

According to one embodiment, it may in particular be a sufficient amount of virucide of natural origin to confer on said information medium incorporating it an antiviral activity greater than 1 log, according to the measuring protocol described in the examples.

For obvious reasons, the amount of virucide of natural origin to be used according to the invention depends in particular on the nature of said virucide and/or on the nature of the information medium, and can therefore vary to a large extent.

Those skilled in the art can, on the basis of their general knowledge, easily determine the appropriate amounts. The adjustment of the amount of virucide of natural origin is part of the competence of those skilled in the art.

By way of illustration, the information medium in accordance with the invention may contain from 0.1 to 2% by dry weight, for example from 0.5 to 1.5% by dry weight, of virucide of natural origin, relative to its total weight.

According to one embodiment, the information medium in accordance with the invention may also contain other additional active compounds, optionally having an antiviral activity.

It may in particular also contain biocides, and for example biocides of bacteriostatic and/or bactericidal and/or fungistatic and/or fungicidal type.

According to another embodiment, the virucide of natural origin required according to the invention may itself have, in addition to its antiviral activity, at least one other biological activity.

Thus, the virucide of natural origin required according to the invention may, for example, also have a bacteriostatic, bactericidal, fungistatic or fungicidal activity, and more particularly a bacteriostatic or bactericidal activity.

Humectant

For the purpose of the invention, a humectant is a compound capable of providing a hydration or else hygroscopic effect.

Against all expectations, the inventors have noted that the presence of such a compound makes it possible to stimulate the antiviral activity of the associated virucide of natural origin, and therefore to increase the antiviral activity exhibited by an information medium in accordance with the invention incorporating these 2 compounds.

By way of representation of these humectants, consideration may be given most particularly, in the context of the present invention, to compounds of polyol type, such as, for example, glycerin, also called glycerol, propylene glycol, polyethylene glycol, butylene glycol, glyceryl triacetate, or else sorbitol.

According to one preferred embodiment variant, the humectant considered is glycerol.

According to another embodiment variant, the humectant considered is chosen from the following compounds:
pidolic acid (PCA) and derivatives thereof (arginine PCA, copper PCA, ethylhexyl PCA, lauryl PCA, magnesium PCA, sodium PCA, zinc PCA, etc.),
calcium gluconate,
fructose, glucose, isomalt, lactose, maltitol, mannitol, polydextrose, sorbitol, sucrose or xylitol,
glycyrrhizic acid and derivatives thereof,
histidine,
hyaluronic acid and salts thereof such as sodium hyaluronate,
silk hydrolysates, keratin hydrolysates or soya hydrolysates,
phytantriol,
silk, or
urea.

The information medium in accordance with the invention may contain from 0.5 to 4% by dry weight, for example from 1 to 3% by dry weight of humectant(s), and in particular of glycerol, relative to its total weight.

According to one preferred embodiment, the humectant is present in the information medium in accordance with the invention in a mass of humectant(s) to mass of virucide(s) weight ratio at least equal to 1.

According to one particular embodiment, the information medium in accordance with the invention may contain at least one virucide according to the present invention, at least one humectant, in particular glycerol, and also at least one bacteriostatic and/or bactericidal biocide or one fungistatic and/or fungicidal biocide.

According to another particular embodiment, the information medium in accordance with the invention may contain at least one virucide according to the present invention, at least one humectant, in particular glycerol, and also at least one bacteriostatic and/or bactericidal biocide and at least one fungistatic and/or fungicidal biocide.

Production Method

Another subject of the invention relates to a method for producing an information medium as defined above.

According to a first embodiment, it is a production method comprising at least the step consisting in bringing a basic medium into contact, in the presence of at least one humectant, with such a virucide of natural origin under conditions suitable for the incorporation thereof at the level of said medium.

In order to be under conditions even more suitable for the incorporation of said virucide of natural origin at the level of said medium, use may be made of particular emulsions or solutions, for example such as ammoniacal solutions or preferably solutions based on 2-amino-2-methyl-1-propanol, which has the advantage of not causing an odor to be given off.

According to one embodiment variant, the humectant may be present in such an emulsion.

The virucide of natural origin may be as defined above, and in particular chosen from monolaurin, lactoferrin and an essential oil having an antiviral activity, for instance bay laurel essential oil.

The humectant may also be as defined above, and in particular be glycerol.

The bringing into contact of said virucide with the basic medium and the incorporation of said virucide in the basic medium can be carried out in various ways:
by immersing said basic medium in a solution of said virucide,
by spraying said basic medium with a solution of said virucide,
by printing said basic medium using an ink containing said virucide,
by surface-treating said basic medium with a preparation containing said virucide and an aqueous surface-treating agent, the aqueous surface-treating agent preferably incorporating glycerol as plasticizer, by layering said basic medium with a layering solution containing said virucide, by depositing onto said basic medium an overprint varnish containing said virucide, and by coating microcapsules or cyclodextrin containing said virucide onto said basic medium.

The humectant is advantageously present in the composition or the solution comprising said virucide.

In particular, said bringing into contact and incorporation of monolaurin can be promoted by using a monolaurin emulsion.

According to another of its aspects, the invention relates to a method for producing an information medium in which at least one virucide of natural origin is synthesized in situ at the level of a basic medium formed, for example, from cellulosic and/or plastic materials.

According to one embodiment variant, this method may also comprise the use of a humectant, in particular as defined above.

This synthesis may in particular be carried out during at least one step of the type of those proposed above for bringing the virucide into contact with the basic medium. In this situation, the bringing into contact is established between the medium and the precursor(s) of the virucide.

The virucide of natural origin may be as defined above, and in particular chosen from monolaurin, lactoferrin and an essential oil having an antiviral activity, for instance bay laurel essential oil.

This embodiment variant is particularly suitable when the virucide of natural origin is, for example, readily accessible by synthesis, preferably at costs that are also advantageous.

Thus, it may, for example, involve monolaurin synthesized in situ by reaction of lauric acid and glycerol in the presence of a catalyst.

Monolaurin is in fact, moreover, commercially available, but at relatively high prices. The synthesis thereof in situ according to this embodiment variant therefore makes it possible to use it in an information medium at a reduced cost.

In particular, said bringing into contact and incorporation of lauric acid can be promoted by using a lauric acid solution, in particular such as an ammoniacal solution or preferably a solution based on 2-amino-2-methyl-1-propanol, which has the advantage of not causing an odor to be given off.

According to this second embodiment, the production method may comprise at least:

a) the depositing at the surface of said basic medium, in the presence of a catalyst, of a composition containing at least lauric acid and glycerol, and b) the subsequent treatment of this medium at a temperature suitable for the synthesis of monolaurin.

According to one embodiment variant, the catalyst is present in the basic medium used in step a).

This variant is in particular suitable when the information medium is in the form of a sheet of paper.

Indeed, the catalyst can be introduced in bulk into the basic fibrous suspension during the sheet formation step, while the lauric acid and the glycerol can be present in a treating solution and thus be introduced at the surface of the medium.

According to another embodiment variant, this catalyst may be present in the composition containing the lauric acid and the glycerol.

Moreover, according to this second embodiment, said basic medium may be a medium based on cellulosic materials, in particular paper, and steps a) and b) can be carried out simultaneously with the steps required for the layering, coating or surface-treating of said basic medium.

In particular, step b) can be carried out simultaneously with the step of drying the layered, coated or surface-treated paper.

This drying step can in particular be carried out at a temperature of greater than or equal to 80° C., for example greater than or equal to 90° C., preferably greater than or equal to 100° C.

This embodiment is particularly advantageous since it makes it possible to incorporate the virucide via a conventional method for producing an information medium, in particular of paper type, i.e. concomitantly with the conventional production steps.

It therefore advantageously does not require any additional step other than those required for producing the medium.

According to one embodiment variant, this method can be carried out in the presence of an antifoam.

More particularly, it is a compound sold under the name Aerotech 3514 (Kemira Chimie SA) and which is formed from a mixture of mineral oils and of nonionic surfactants.

Such a compound can be introduced at a concentration of between 0.01% and 0.30%, preferably between 0.04% and 0.20%, and more preferentially between 0.04% and 0.12%, relative to the total weight of the mixture of lauric acid and glycerol.

As indicated above, the synthesis of monolaurin from lauric acid and glycerol is carried out in the presence of a catalyst.

By way of example of a catalyst that is more particularly suitable for catalyzing this reaction, mention may in particular be made of zeolites, and for example the zeolite A sold by the company FMC Foret, or lipases.

When the catalyst is a lipase, reference may in particular be made to the reaction conditions described by Pereira C. C. B., Da Silva M. A. P. and Langone M. A. P. in the publication "*Enzymatic synthesis of monolaurin*" (Applied biochemistry and Biotechnology, 2004, vol. 113-116, p. 433-445).

By way of lipase that is more particularly suitable in the context of the present invention, mention may, for example, be made of the lipases sold under the references Liposyme RM IM®, Lipozyme TL IM®, and Resinase A2C® by the company Novozymes.

The information medium in accordance with the invention may contain from 0.5 to 3% by dry weight, for example from 0.5 to 2% by dry weight, of catalyst, relative to its total weight.

The catalyst, for example the zeolite, may be introduced in a proportion of at least 2% by weight, for example at least 5% by weight, relative to the total weight of the mixture of lauric acid and glycerol.

According to a first embodiment variant, the lauric acid and the glycerol may be introduced as an equimolar mixture.

According to a second embodiment variant, the glycerol may be introduced in excess relative to the lauric acid.

According to this second variant, residual excess glycerol therefore remains present in the medium at the end of the reaction.

As mentioned above, this residual glycerol can play the role of a humectant and increase the antiviral properties.

An example of a method for preparing monolaurin in situ is represented in example 3 hereinafter.

The following nonlimiting examples will make it possible to understand more clearly how the invention can be put into practice and the advantages thereof.

EXAMPLES

Comparative Example 1

A sheet of paper is formed on a papermaking machine called a cylinder mold with a wire cloth comprising a pattern allowing a watermark to be produced, it being possible for this paper to be suitable as a paper for producing a banknote, in the following manner:
- a cotton fiber pulp is suspended in water, and this suspension is refined to 60° Schoepper-Riegler,
- a wet-strength agent is added, approximately 2.5% by dry weight of a poly(aminoamide epichlorohydrin) resin, expressed relative to the cotton fibers,
- iridescent planchettes are also introduced into this suspension,
- during the formation of the sheet, a microprinted security thread, called a "window thread" is introduced according to known prior techniques so as to make this thread visible in certain windows at the surface of the paper. One method that can be used to introduce this thread is described, for example, in patent EP 0 059 056, and the sheet is dried at around 100° C.

Example 2

A medium is obtained as in example 1, and is coated with a preparation made in an aqueous medium which comprises:
- 31.2 parts by dry weight of glycerol,
- 18.8 parts by dry weight of lactoferrin,
- 31.2 parts by dry weight of a PVA binder, and
- 18.8 parts by dry weight of zeolite (zeolite A).

The concentration of lactoferrin relative to the total layering solution is set at 4.7% by weight.

Once coated, the paper comprises a content by dry weight of lactoferrin of approximately 0.98 g/m$^2$.

Example 3

A medium is obtained as in example 1, and is coated with a preparation made in an aqueous medium which comprises:
- 31.2 parts by dry weight of glycerol,
- 18.8 parts by dry weight of lauric acid,
- 31.2 parts by dry weight of a PVA binder, and
- 18.8 parts by dry weight of zeolite (zeolite A).

The concentrations of glycerol and of lauric acid relative to the total layering solution are set, respectively, at 6.24 and 3.76% by weight.

Once coated, the paper comprises a content by dry weight of monolaurin of approximately 1.03 g/m$^2$.

Example 4

A medium is obtained as in example 1, and is coated with a preparation made in an aqueous medium which comprises:
- 31.2 parts by dry weight of glycerol,
- 18.8 parts by dry weight of monolaurin,
- 31.2 parts by dry weight of a PVA binder, and
- 18.8 parts by dry weight of zeolite (zeolite A).

The concentration of monolaurin relative to the total layering solution is set at 3.76% by weight.

Once coated, the paper comprises a content by dry weight of monolaurin of approximately 1.13 g/m$^2$.

Example 5

A medium is obtained as in example 1, and is coated with a preparation made in a dispersion of polyurethanes which comprises:
- 56.4 parts by dry weight of polyurethane,
- 5.6 parts by dry weight of colloidal silica,
- 33.8 parts by dry weight of glycerol,
- 3.8 parts by dry weight of noble laurel essential oil, and
- 0.4 part by dry weight of emulsifier (fatty alcohol ethoxylate).

The concentration of bay laurel essential oil relative to the total layering solution is set at 1.6% by weight.

The pH of the layering solution is fixed at 8.4.

Once coated, the paper comprises a content by dry weight of noble bay laurel essential oil of approximately 0.19 g/m$^2$.

Example 6

A medium is obtained as in example 1, and is impregnated with a preparation made in an aqueous medium which comprises:
- 40 kg of PVA binder, The PVAs are cured and water is added for a final volume of 950 l;
- 25 kg of glycerol;
- 20 kg of lauric acid;
- 2 kg of zeolite (zeolite A); and
- 10 l of AMP90.

Tests and Results

1. Anti-Phage Activity

The anti-phage activity test, which is the applicant's own test, is based on modified standard JIS L 1902, or else on modified standard ISO 20743, on MS2 phages, which are reputed to be very resistant, and applied over action times of between 18 and 24 hours.

The principle is the following: MS2 phages are deposited on the test media, and then the number of active MS2 phages is evaluated a first time at t=0 h, and a second time at t=24 h.

In order to evaluate the number of active MS2 phages on the test media at a given time, these media are placed in the presence of particular bacteria which have the property of being hosts for MS2 phages: measurement of the number of lysis plaques (or pfp) after culture then makes it possible to work back to the desired amount of MS2 phages.

It is thus possible to deduce therefrom an anti-phage activity (denoted A), defined as follows:

$$A = [\text{mean log}(C_{24}) - \text{mean log}(C_0)] - [\text{mean log}(E_{24}) - \text{mean log}(E_0)],$$

in which formula, $E_{24}$ corresponds to the number of lysis plaques at 24 h and $E_0$ corresponds to the number of lysis plaques just after it has been brought into contact with the medium tested.

The experimental conditions are the following:
- The diluent used is peptone/salt (having the Difco reference 1897-17) and the bacterial strain used is *Escherichia coli* K12, which is a host strain for MS2 phages.
- The control medium is an untreated 100% cotton textile.
- 200 µl of a suspension of phages at 1×10$^5$ pfp/ml are deposited.

The results are reported hereinafter.

Examples 2 to 4

| Sample ref. | test piece | $C_0$ (pfp/g) | 0 h | | | 24 h | | | |
|---|---|---|---|---|---|---|---|---|---|
| | | | $\log(C_0)$ | Standard deviation | mean log $(C_0)$ | $C_{24}$ (pfp/g) | $\log(C_{24})$ | Standard deviation | mean log $(C_{24})$ |
| Control | 1 | 256 000 | 5.41 | 0.07 | 5.36 | 38 600 | 4.59 | 0.00 | 4.59 |
| | 2 | 207 000 | 5.32 | | | 39 100 | 4.59 | | |

| Sample ref. | test piece | $E_0$ (pfp/g) | 0 h | | | 24 h | | | |
|---|---|---|---|---|---|---|---|---|---|
| | | | $\log(E_0)$ | Standard deviation | mean log $(E_0)$ | $E_{24}$ (pfp/g) | $\log(E_{24})$ | Standard deviation | mean log $(E_{24})$ |
| Example 2 | 1 | 84 000 | 4.92 | 0.01 | 4.92 | 800 | 2.90 | 0.21 | 2.75 |
| | 2 | 82 000 | 4.91 | | | 400 | 2.60 | | |
| Example 3 | 1 | 223 000 | 5.35 | 0.15 | 5.24 | 1 370 | 3.14 | 0.08 | 3.19 |
| | 2 | 136 000 | 5.13 | | | 1 760 | 3.25 | | |
| Example 4 | 1 | 74 000 | 4.87 | 0.11 | 4.95 | 1 100 | 3.04 | 0.08 | 2.98 |
| | 2 | 106 000 | 5.03 | | | 840 | 2.92 | | |

The following anti-phage activities are deduced therefrom:

$$A_{example\ 2} = -0.77-(-2.17) = 1.40\ \log$$

$$A_{example\ 3} = -0.77-(-2.05) = 1.28\ \log$$

$$A_{example\ 4} = -0.77-(-1.97) = 1.20\ \log$$

Example 5

| Sample ref. | test piece | $C_0$ (pfp/g) | 0 h | | | 24 h | | | |
|---|---|---|---|---|---|---|---|---|---|
| | | | $\log(C_0)$ | Standard deviation | mean log $(C_0)$ | $C_{24}$ (pfp/g) | $\log(C_{24})$ | Standard deviation | mean log $(C_{24})$ |
| Control | 1 | 2 728 000 | 6.44 | 0.05 | 6.47 | 830 000 | 5.92 | 0.15 | 6.02 |
| | 2 | 3 160 000 | 6.50 | | | 1 350 000 | 6.13 | | |

| Sample ref. | test piece | $E_0$ (pfp/g) | 0 h | | | 24 h | | | |
|---|---|---|---|---|---|---|---|---|---|
| | | | $\log(E_0)$ | Standard deviation | mean log $(E_0)$ | $E_{24}$ (pfp/g) | $\log(E_{24})$ | Standard deviation | mean log $(E_{24})$ |
| Example 5 | 1 | 1 735 000 | 6.24 | 0.01 | 6.24 | 35 000 | 4.54 | 0.19 | 4.68 |
| | 2 | 1 772 000 | 6.25 | | | 64 000 | 4.81 | | |

The following anti-phage activity is likewise deduced therefrom:

$$A_{example\ 5} = 0.45-(-1.56) = 1.11\ \log.$$

These tests then consequently demonstrate that the media obtained in accordance with the invention actually exhibit a significant antiviral activity.

Example 6

| Sample ref. | test piece | $C_0$ (pfp/g) | log ($C_0$) | 0 h Standard deviation | mean log ($C_0$) | $C_{24}$ (pfp/g) | log ($C_{24}$) | 24 h Standard deviation | mean log ($C_{24}$) |
|---|---|---|---|---|---|---|---|---|---|
| Control | 1 | 17 000 | 4.23 | 0.12 | 4.31 | 5 400 | 3.73 | 0.19 | 3.60 |
|  | 2 | 25 000 | 4.40 |  |  | 2 900 | 3.46 |  |  |

| Sample ref. | test piece | $E_0$ (pfp/g) | log ($E_0$) | 0 h Standard deviation | mean log ($E_0$) | $E_{24}$ (pfp/g) | log ($E_{24}$) | 24 h Standard deviation | mean log ($E_{24}$) |
|---|---|---|---|---|---|---|---|---|---|
| Example 6 | 1 | 23 000 | 4.36 | 0.00 | 4.36 | 0 | — | — | Heterogeneous results |
|  | 2 | 23 000 | 4.36 |  |  | 60 | 1.78 |  |  |

From the values presented above, it may be noted that test piece 1 is totally phagicidal, and the anti-phage activity of test piece 2 can be calculated as follows:

$A_{example\ 6} = 0.71 - (-2.58) = 1.87$ log.

These tests consequently demonstrate that the media obtained in accordance with the invention actually exhibit a significant antiviral activity.

2. Bactericidal/Bacteriostatic Activity

Antibacterial tests were also carried out on the information medium obtained according to example 6, using 2 bacterial strains, namely *Staphylococcus aureus* CIP 4.83 and *Klebsiella pneumoniae* 368 CIP.

The bactericidal/bacteriostatic activity test, which is the applicant's own test, is based on standard ISO 20743 and applied over action times of between 18 and 24 hours.

The principle is the following: the bacteria are inoculated by transfer onto the test medium, and then the number of bacterial colonies is measured a first time at t=0 h and a second time at t=24 h.

In order to evaluate the number of bacterial colonies remaining on the test media at a given time, they are counted using a plaque counting method.

It is possible to deduce therefrom the growth value of the tests (denoted G), defined as follows:

$F(\log_{10}) = \text{mean log } T_{t24} - \text{mean log } T_0$ in which formula, $T_{t24}$ corresponds to the number of bacterial colonies at 24 h and $T_0$ corresponds to the number of bacterial colonies just after they have been brought into contact with the medium tested.

The value of the growth of control comparative strains (denoted F) is also determined, and defined as follows:

$F(\log_{10}) = \text{mean log } C_{t24} - \text{mean log } C_0$ in which formula, $C_{t24}$ corresponds to the number of bacterial colonies at 24 h and $C_0$ corresponds to the number of bacterial colonies just after they have been brought into contact with the control medium.

It is thus possible to deduce therefrom the value of the bacterial activity (denoted A), defined as follows:

$A(\log_{10}) = F - G$

The experimental conditions are the following:

The diluent used is peptone/salt (having the Difco reference 218971) and the bacterial strain used is either *Staphylococcus aureus* CIP 4.83, or *Klebsiella pneumoniae* 368 CIP.

The concentration of the inoculum for *Staphylococcus aureus* is $3.8 \times 10^5$ CFU/ml. The concentration of the inoculum for *Klebsiella pneumoniae* is $1.23 \times 10^6$ CFU/ml.

The control medium is an untreated 100% cotton textile.

The results are reported hereinafter.

*Staphylococcus aureus*

| Sample ref. | test piece | $C_0$ (CFU) | log ($C_0$) | 0 h mean log ($C_0$) | $C_{t24}$ (CFU) | log ($C_{t24}$) | 24 h mean log ($C_{t24}$) |
|---|---|---|---|---|---|---|---|
| Control: 100% cotton textile | 1 | 36 000 | 4.56 | 4.45 | 23 500 000 | 7.37 | 7.42 |
|  | 2 | 21 600 | 4.33 |  | 29 800 000 | 7.47 |  |

| Sample ref. | test piece | $T_0$ (CFU) | log ($T_0$) | 0 h mean log ($T_0$) | $T_{t24}$ (CFU) | log ($T_{t24}$) | 24 h mean log ($T_{t24}$) |
|---|---|---|---|---|---|---|---|
| Example 6 | 1 | 52 000 | 4.72 | 4.62 | 1 270 | 3.10 | 2.64 |
|  | 2 | 33 000 | 4.52 |  | 150 | 2.18 |  |

The following antibacterial activity is deduced therefrom:

$A(\log_{10}) = 4.95$.

These tests consequently demonstrate that the media obtained in accordance with the invention can also have, in addition to a significant antiviral activity, a significant bactericidal activity.

| | | *Klebsiella pneumoniae* | | | | | |
|---|---|---|---|---|---|---|---|
| | | Incubation time | | | | | |
| | | 0 h | | | 24 h | | |
| Sample ref. | test piece | $C_0$ (CFU) | log ($C_0$) | mean log ($C_0$) | $C_{t24}$ (CFU) | log ($C_{t24}$) | mean log ($C_{t24}$) |
| Control: 100% cotton textile | 1 | 45 000 | 4.65 | 4.55 | 16 100 000 | 7.21 | 7.10 |
| | 2 | 27 900 | 4.45 | | 10 000 000 | 7.00 | |

| | | Incubation time | | | | | |
|---|---|---|---|---|---|---|---|
| | | 0 h | | | 24 h | | |
| Sample ref. | test piece | $T_0$ (CFU) | log ($T_0$) | mean log ($T_0$) | $T_{t24}$ (CFU) | log ($T_{t24}$) | mean log ($T_{t24}$) |
| Example 6 | 1 | 57 000 | 4.76 | 4.82 | 0 | — | — |
| | 2 | 75 000 | 4.88 | | 0 | — | |

It can be noted that the two test pieces have a bactericidal activity.

These tests consequently demonstrate that the media obtained in accordance with the invention can also have, in addition to a significant antiviral activity, a significant bactericidal activity.

The present examples above are obviously not exhaustive and other basic media and other virucidal agents may be envisioned without departing from the field of protection of the patent.

In particular, the basic medium may be a high-durability security paper which is the subject of patent application FR 2 814 476, a printing/writing paper, tracing paper or a plastic ticket.

The invention claimed is:

1. A method for producing an information medium having antiviral activity, the method comprising:
   in the presence of a catalyst, depositing on a surface of a substrate medium an aqueous composition comprising at least lauric acid and glycerol, the substrate medium comprising paper, and the catalyst selected from the group consisting of a zeolite catalyst and a lipase catalyst; and
   subsequent to depositing the aqueous composition and in the presence of the catalyst, heating the substrate medium with the aqueous composition deposited thereon, wherein the heating:
   comprises subjecting the substrate medium to a temperature of approximately 80° C. to approximately 100° C.,
   synthesizes monolaurin, in situ on the substrate medium, from the lauric acid and glycerol, and
   dries the substrate medium and the monolaurin synthesized thereon.

2. The method of claim 1, wherein the catalyst is present in the substrate medium prior to deposition of the aqueous composition.

3. The method of claim 1, wherein the catalyst is present in the aqueous composition prior to deposition of the aqueous composition.

4. The method of claim 3, wherein the catalyst is present in the aqueous composition in a proportion of at least 2% by weight relative to a total weight of the lauric acid and the glycerol.

5. The method of claim 1, wherein heating the substrate medium comprises subjecting the substrate medium to a temperature of approximately 90° C. to approximately 100° C.

6. The method of claim 5, wherein heating the substrate medium comprises subjecting the substrate medium to a temperature of approximately 100° C.

7. The method of claim 1, wherein the glycerol is in molar excess over the lauric acid.

8. The method of claim 1, further comprising, prior to deposition of the aqueous composition, forming the substrate medium.

9. The method of claim 8, further comprising introducing the catalyst into the substrate medium during the formation of the substrate medium.

10. The method of claim 1, wherein the information medium produced has an antiviral activity of greater than 1 log.

11. The method of claim 1, wherein the substrate medium comprises a security element chosen from one or more of a security thread, a watermark, a pattern, a patch, a foil, a planchette, a strip, a printed thread, a metalized thread, and a particle.

12. The method of claim 11, wherein the security element is detectable using one or more of ultraviolet radiation, infrared radiation, visible light, electricity, and magnetism.

13. The method of claim 1, wherein the substrate medium comprises cellulose fibers.

14. The method of claim 1, wherein the substrate medium comprises cotton fibers.

\* \* \* \* \*